United States Patent
Wojke et al.

(10) Patent No.: US 10,532,147 B2
(45) Date of Patent: Jan. 14, 2020

(54) METHOD OF FLUSHING AN EXTRACORPOREAL BLOOD CIRCUIT

(71) Applicant: FRESENIUS MEDICAL CARE DEUTSCHLAND GMBH, Bad Homburg (DE)

(72) Inventors: Ralf Wojke, Bad Homburg (DE); Paul Wieneke, Muenster (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 0 days.

(21) Appl. No.: 15/501,552

(22) PCT Filed: Aug. 5, 2015

(86) PCT No.: PCT/EP2015/001619
§ 371 (c)(1),
(2) Date: Feb. 3, 2017

(87) PCT Pub. No.: WO2016/020062
PCT Pub. Date: Feb. 11, 2016

(65) Prior Publication Data
US 2017/0224902 A1    Aug. 10, 2017

(30) Foreign Application Priority Data
Aug. 5, 2014  (DE) .................. 10 2014 011 671

(51) Int. Cl.
*A61M 1/36* (2006.01)
*A61M 39/28* (2006.01)

(52) U.S. Cl.
CPC ........ *A61M 1/3673* (2014.02); *A61M 1/3643* (2013.01); *A61M 1/3644* (2014.02); *A61M 39/28* (2013.01); *A61M 2202/0478* (2013.01)

(58) Field of Classification Search
None
See application file for complete search history.

(56) References Cited

U.S. PATENT DOCUMENTS

| | | | | |
|---|---|---|---|---|
| 5,650,071 A | * | 7/1997 | Brugger | A61M 1/3643 210/646 |
| 2009/0004053 A1 | | 1/2009 | Kenley | |
| 2011/0237996 A1 | | 9/2011 | Kotanko et al. | |

FOREIGN PATENT DOCUMENTS

| | | |
|---|---|---|
| DE | 3879127 | 6/1993 |
| DE | 19704564 | 8/1998 |

OTHER PUBLICATIONS

Mujais, Salim et al—Heparin Free Hemodialysis Using Heparin Coated Hemophan—ASAIO Journal, 1996 (Year: 1996).*

(Continued)

*Primary Examiner* — Bradley R Spies
(74) *Attorney, Agent, or Firm* — Jacobson Holman, PLLC.

(57) ABSTRACT

The invention relates to a method of flushing an extracorporeal blood circuit, preferably an extracorporeal blood circuit of a dialysis machine, with a flushing liquid, wherein the flushing liquid contains an anticoagulant agent, preferably heparin. The invention further relates to an extracorporeal blood treatment unit, preferably to a dialysis machine, having an extracorporeal blood circuit and a control unit, wherein the control unit is configured to carry out a flushing method in accordance with one of the preceding claims before the start of the treatment and/or intermittently during the treatment.

11 Claims, 2 Drawing Sheets

(56) References Cited

OTHER PUBLICATIONS

Figure 1:
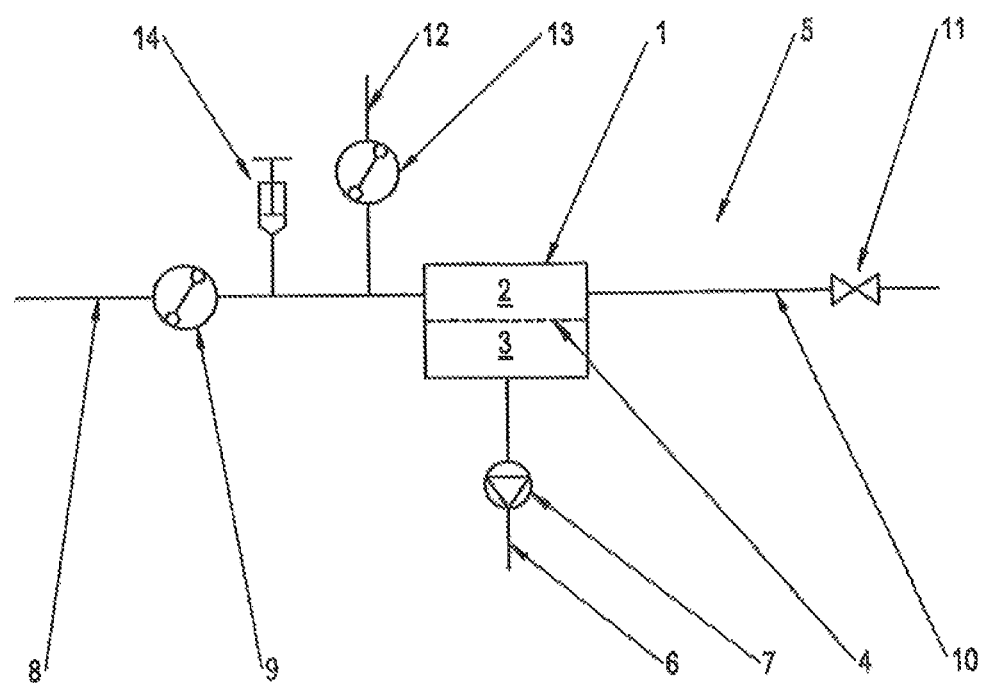

Lavaud, Sylvie et al—Optimal anticoagulation strategy in haemodialysis with heparin-coated polyacrylonitrile membrane—Nephrology Dialysis Transplantation—2003 (Year: 2003).*

Mujais et al. Heparin Free Hemodialysis Using Heparin Coated Hemophan. Asaio Journal, vol. 42, No. 5, Sep. 1, 1996, p. M538-M541.

* cited by examiner

METHOD OF FLUSHING AN EXTRACORPOREAL BLOOD CIRCUIT

The invention relates to a method of flushing an extracorporeal blood circuit with a flushing liquid and to an extracorporeal blood treatment unit having an extracorporeal blood circuit and a control unit.

The avoidance of the formation of blood clots in the extracorporeal blood circuit is a central objective in extracorporeal blood treatment. Different solution concepts are generally conceivable.

A possibility is to dispense an anticoagulant agent such as heparin to the patient, for example by injection of heparin into the extracorporeal blood circuit. This has the advantage of a continuous and efficient coagulation inhibition, but has the disadvantage inter alia also of a high heparin dosage dispensed to the patient.

There is furthermore the possibility of flushing the extracorporeal blood circuit before the start of the treatment with an anticoagulant agent which is intended to adhere to the surface of the circuit. This has the advantage of a small heparin dosage dispensed to the patient, but has the disadvantage that the effectiveness decreases as the length of treatment increases and is ultimately substantially lost. There is furthermore the possibility of also flushing the circuit during the treatment with a solution containing an anticoagulant agent. This has the advantage of a periodic refreshing of the anticoagulation effect, but has the disadvantage of a complicated process management.

The two last-named alternatives are, however, less efficient in general in comparison with the dispensing of heparin to the patient as relates to the avoidance of the formation of clots. However, a dialysis treatment free of heparin or at least with reduced heparin is aimed for in up to 7% of the patients suffering from acute renal failure or from ESRD for various medical reasons.

It is the underlying object of the invention to reduce the quantity of anticoagulant agents which are systemically effectively dispensed to the patient and simultaneously to efficiently avoid the formation of clots in the extracorporeal blood circuit.

Against this background, the invention relates to a method of flushing an extracorporeal blood circuit with a flushing liquid, wherein the flushing liquid contains an anticoagulant agent.

In this manner, the anticoagulant agent is intended to contact the hose walls of the extracorporeal blood circuit and the membranes of the dialyzer so that it can adhere and can prevent the formation of clots over a certain treatment time.

The extracorporeal blood circuit is preferably that of a dialysis machine. Furthermore, a use of the method is also conceivable in other extracorporeal treatment systems, for example in ultrafiltration devices and heart-lung machines.

In an embodiment, the anticoagulant agent is heparin. Heparin is particularly effective and highly compatible so that it is used very frequently in medicine. Furthermore, provided it is introduced into the extracorporeal blood circuit within the framework of the method in accordance with the invention, the heparin adheres sufficiently to the hose walls of the extracorporeal blood circuit and to the dialyzer to prevent the formation of clots over a certain treatment time.

In an embodiment, the extracorporeal circuit is completely filled with the flushing liquid. It can thus be ensured that all parts of the extracorporeal blood circuit come into contact with the flushing liquid and with the anticoagulant agent.

In an embodiment, the flushing liquid remains stationary in the circuit for a certain dwell time. This effects a stronger adhesion with a smaller consumption than in a passage operation, for example. Suitable dwell times with common intervals and concentrations of the anticoagulant agent amount, for example, to between 4 and 15 minutes or to between 8 and 12 minutes. In an embodiment, the flushing liquid is moved during the dwell time, for example is conveyed to and fro, or is circulated in a short-circuited circuit.

In an embodiment, the flushing liquid is displaced out of the circuit at the end of the dwell time. It is thereby prevented that flushing liquid which contains an anticoagulant agent moves into the bloodstream of the patient in the further procedure and thus that an anticoagulant agent is inherently dispensed to the patient. To this extent, the displacement can take place using a flushing liquid which is free of the anticoagulant agent. Provided that the method is carried out intermittently during a treatment, the displacement can also take place using blood.

In an embodiment, the procedures of the remaining of the flushing liquid in the circuit and the subsequent displacement are repeated at least twice and optionally several times. It can be meaningful in this case to carry out the displacement with a flushing liquid which likewise contains an anticoagulant agent, preferably heparin. An optional multiple repetition of the procedure can improve the result with respect to coagulation inhibition.

In an embodiment, at least some of the flushing liquid leaves the extracorporeal circuit through an outflow which differs from the venous port. The quantity of flushing liquid conducted back to the patient and the quantity of anticoagulant agent conducted back to the patient can thus be reduced on an intermittent process management during the treatment.

In an embodiment, the extracorporeal blood circuit comprises a dialyzer and the outflow corresponds to the dialyzer. A use of the dialyzer as an outflow can in particular be provided when the flushing process is carried out on a hemodiafiltration unit or a hemofiltration unit.

In an embodiment, the outflow is arranged in the venous line. The outflow is preferably close to the venous port. This simplifies a process management which only returns a small residual quantity of the flushing solution and of the anticoagulating agent to the patient.

In an embodiment, the extracorporeal blood circuit has a venous clamp which is closed at least at times during the process. The term of a clamp in the present case also comprises a blocking valve or a three-way valve. The valves can, for example, be operated using a central control unit by means of actuators. The venous clamp is preferably arranged between the outflow and the venous port. The outflow can likewise have a clamp which is closed at times during the process, with the clamp being able to be open at the start of the process in the filling phase and at the end of the process in the displacement phase.

In an embodiment, at least some of the flushing liquid flows through an inflow into the extracorporeal blood circuit which differs from the arterial port. This inflow can be arranged in the arterial line. In an embodiment, the inflow is arranged upstream of the blood pump. The inflow can alternatively be arranged downstream of the blood pump. In an embodiment, existing interfaces are used as the inflow, for example a predilution port.

In an embodiment, the flushing liquid is admixed with the anticoagulant agent before or after its entry into the extracorporeal blood circuit. For example, the anticoagulant agent can be added to the flushing liquid from a separate reservoir directly before or on the introduction into the extracorporeal blood circuit.

In an embodiment, the method can be carried out before the start of the extracorporeal blood treatment within the framework of the priming of the extracorporeal blood circuit and can, for example, represent the concluding step of the priming process. The extracorporeal circuit can be filled predialytically (possibly in a circulating manner), for example via program control with a substitution solution heparinized by a heparin pump and can be flushed out e.g. with dialyzate after a predefined dwell time. This process can be carried out once or several times. A heparinized surface is automatically produced in the extracorporeal circuit.

Alternatively or additionally, an intermittent process management is possible during the extracorporeal blood treatment. In this case, a possible process management can comprise the following steps: (a) Holding the blood pump and opening a previously closed separate inflow; (b) Complete filling of at least one portion of the extracorporeal blood circuit with a flushing liquid which contains an anticoagulant agent; (c) Closing the inflow and a previously open venous clamp; (d) Waiting through a dwell time; (e) Opening a previously closed separate outflow which is arranged in the venous line; (f) Starting the blood pump and displacing the flushing liquid; (g) Closing the outflow and opening the venous clamp; (h) Continuing the treatment. In this case, the inflow is preferably arranged downstream of the blood pump.

The invention further relates to an extracorporeal blood treatment unit, having an extracorporeal blood circuit and a control unit, wherein the control unit is configured to carry out a flushing method in accordance with the invention before the start of the treatment and/or intermittently during the treatment.

The feature that the control unit is configured to carry out a method in accordance with one of the preceding claims means that a corresponding routine is stored in the control unit and that the control unit is connected to the necessary actuators (e.g. pumps and valves) which are required for carrying out the method.

In an embodiment, the extracorporeal blood treatment unit is a dialysis machine. The dialysis machine can be suitable and intended for carrying out a hemodialysis, a hemodiafiltration, a hemofiltration and/or an ultrafiltration (only liquid removal). Furthermore, the extracorporeal blood treatment unit in accordance with the invention can be another treatment system, for example an ultrafiltration device or a heart-lung machine. The extracorporeal blood treatment unit can comprise constructional features which were described in connection with the method in accordance with the invention. The extracorporeal blood circuit can, for example, have an outflow for flushing liquid which differs from the venous port of the extracorporeal blood circuit.

In an embodiment, the control unit is configured so that it automatically interrupts the treatment before carrying out the intermittent flushing process. The triggering and the control of the flushing process take place automatically by means of the routine stored in the control unit. An interruption can take place, for example, in response to specific sensor reports which allow a conclusion of an incipient clogging of the filter.

In an embodiment, the control unit is configured so that it automatically continues the treatment after carrying out the intermittent flushing process.

In an embodiment, the control unit is configured so that it activates the intermittent flushing process at periodic time intervals during the treatment, with the time intervals preferably being between 30 minutes and 2 hours. Empirical values show that the anticoagulant effect decreases considerably after a preceding flushing with an anticoagulant agent after 2 hours at the latest so that it is meaningful to select the intervals as less than 2 hours. At the same time, an interruption of the treatment in time intervals which are less than 30 minutes is not proportionate.

In an embodiment, the control unit is configured so that it takes account of the quantity of flushing liquid supplied by the process and/or of blood led off by the process in the determination of treatment-specific parameters, in particular in the determination of the ultrafiltration volume.

The blood pump and/or the flushing pump can be a peristaltic pump, for example a fully occluding roller pump. The flushing liquid can, for example, be a substitution solution or a priming solution. Examples comprise physiological saline and Ringer's solution. The solution can furthermore optionally contain anticoagulation means such as heparin.

Figure 2:
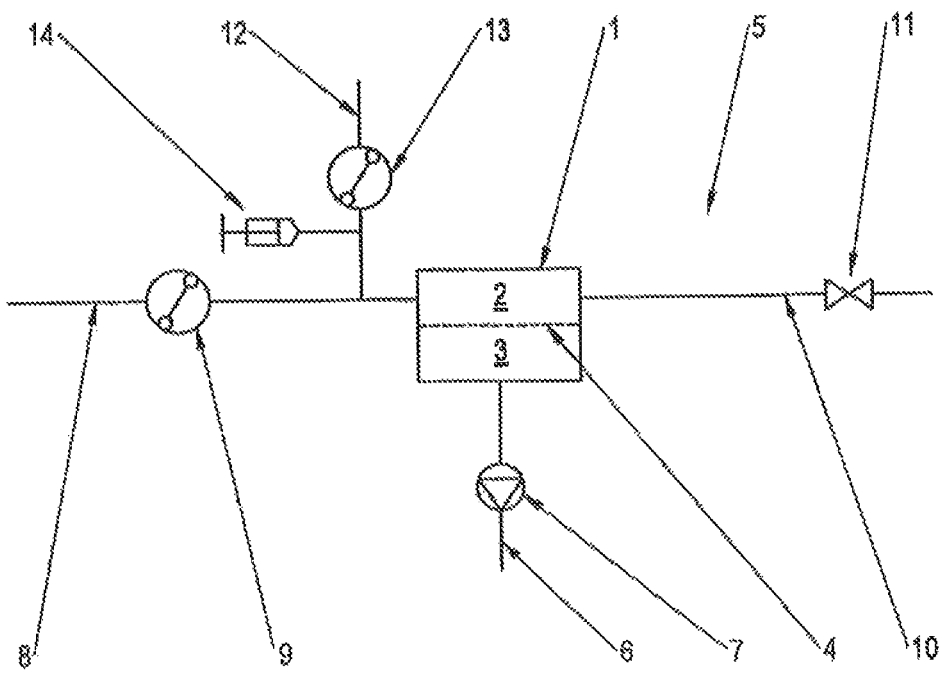
Figure 3:
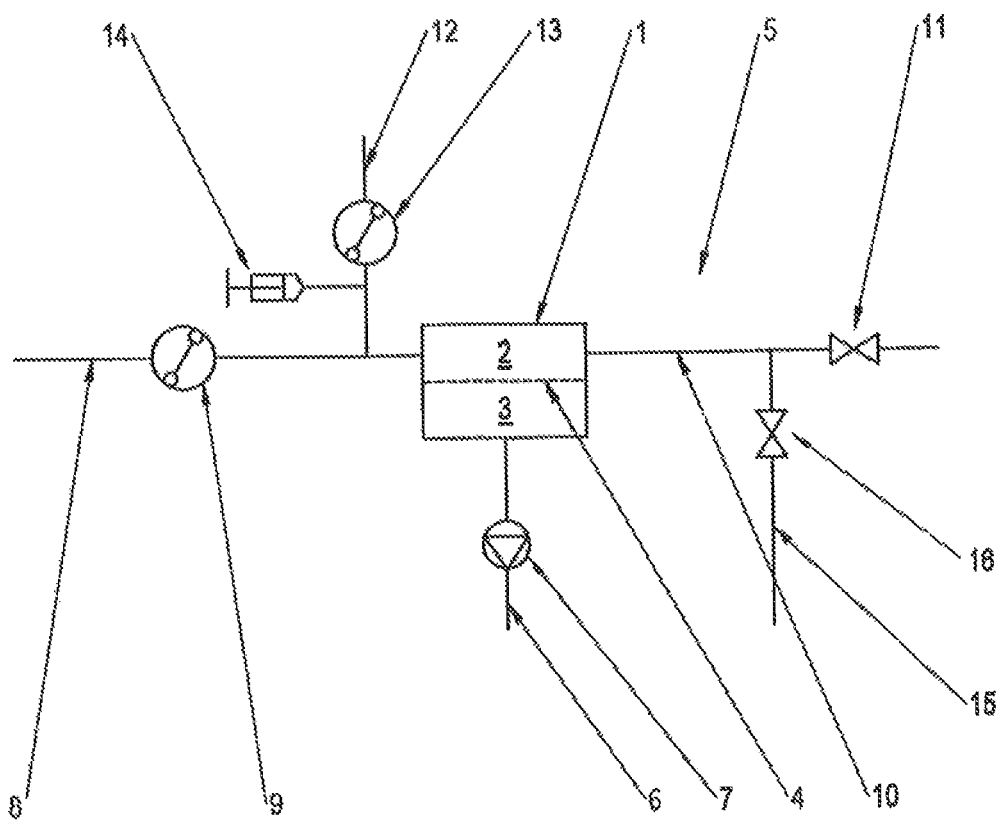

Further details and advantages result from the Figures and embodiments described in the following. There are shown in the Figures:

FIG. 1: a schematic representation of fluid circuits in accordance with a dialysis machine in accordance with a first embodiment of the invention;

FIG. 2: a schematic representation of fluid circuits in accordance with a dialysis machine in accordance with a second embodiment of the invention; and FIG. 3: a schematic representation of fluids circuits in accordance with a dialysis machine in accordance with a third embodiment of the invention.

FIG. 1 shows a schematic representation of fluid circuits in accordance with a dialysis machine in accordance with a first embodiment of the invention. The dialysis machine has a dialyzer 1 which has a blood chamber 2 and a dialyzate chamber 3 which are separated from one another by a membrane 4. The blood chamber 2 is a component of an extracorporeal blood circuit 5. The dialyzate chamber 3 is connected to an outflow 6 for dialyzate in which an ultrafiltration pump 7 is arranged. Any further lines connected to the dialyzate chamber such as a dialysis liquid source are not shown in the illustration, but can nevertheless be provided. The blood circuit 5 has an arterial line 8, with a blood pump 9, and a venous line 10 which are connected to the blood side of the dialyzer. A venous clamp 11 is located at the downstream end of the venous line.

A predilution line 12 with a substitution pump 13 opens into the arterial line downstream of the blood pump. Furthermore, a heparin pump 14 is provided which starts at the arterial line between the blood pump 9 and the predilution line. A different positioning of the predilution line and of the heparin pump is naturally also possible and covered by the invention.

A method in accordance with the invention can be carried out as follows before the start of the treatment: The arterial line and the venous line are not connected to the patient. The extracorporeal blood circuit is filled completely with physiological flushing solution, for example using the predilution line or through the arterial line or venous line and the arterial line and the venous line are subsequently short-circuited. Heparin is added to the solution in the circuit using the heparin pump. The solution is subsequently circulated for 10 minutes. After the end of this method step, the short-circuit is released and the flushing solution containing heparin is displaced by fresh flushing solution, with the fresh flushing solution being able to penetrate into the circuit, for example through the predilution line or through the arterial line, and with the flushing solution containing heparin being able to be removed from the circuit, for example through the venous line. The process can optionally be repeated, i.e. the arterial and venous lines can again be short-circuited, heparin can again be injected and the solution can again be circulated.

FIG. 2 shows a schematic representation of liquid circuits in accordance with a dialysis machine in accordance with a second embodiment of the invention. Components already known from FIG. 1 are provided with corresponding reference numerals.

This embodiment differs from the embodiment shown in FIG. 1 in that the heparin pump 14 opens into the predilution line 12 and not into the arterial line. The flushing liquid can thus already be heparinized before entering into the extracorporeal blood circuit.

An example of an intermittent carrying out of the method in accordance with the invention during a dialysis treatment will be illustrated in the following with reference to this embodiment. After periodic time intervals of 90 minutes, a flushing process in accordance with the invention is carried out automatically by the control unit during the treatment. For this purpose, the substitution pump 13 is activated and the blood pump is held. The flushing liquid is heparinized before entering into the extracorporeal circuit via the line 12 by means of the heparin pump 14. As soon as the part of the extracorporeal blood circuit located downstream of the opening point of line 12 is filled with heparinized flushing liquid, the substitution pump is likewise held, the venous clamp 11 is closed and the solution is held stationary in the circuit for 10 minutes. Subsequently, the venous clamp is opened, the blood pump is activated and the treatment is continued. A long dwell time of the heparin can thus be achieved with a moderate heparin dispensing to the patient.

FIG. 3 shows a schematic representation of fluid circuits in accordance with a dialysis machine in accordance with a third embodiment of the invention. Components already known from FIGS. 1 and 2 are provided with corresponding reference numerals.

This embodiment differs from the embodiment shown in FIG. 2 in that the extracorporeal blood circuit furthermore has a separate outflow 15 for the flushing liquid. It is thus made possible that flushing liquid cannot flow off via the venous line, but rather via the separate outflow 15. At the inlet side, the separate outflow 15 has a clamp 16.

A further example of an intermitting carrying out of the method in accordance with the invention during a dialysis treatment will be illustrated in the following with reference to this embodiment. This example differs from the preceding example in that it is not the venous clamp 11 which is opened after the dwell time of the heparinized solution in the extracorporeal blood circuit, but rather the outflow clamp 16. The blood pump is then activated until the heparinized flushing solution has been displaced via the outflow 15 out of the circuit and the blood has approximately arrived in the region of the opening of the outflow. This can be detected using suitable sensors. The outflow clamp 16 is subsequently closed, the venous clamp 11 opened and the treatment continued. A long dwell time of the heparin can thus be achieved with a low heparin consumption and a heparin dispensing to the patient can be largely avoided despite a treatment-intermittent process management.

A separate outflow in the venous branch can be helpful both in the predialytic flushing and in the intradialytic flushing. The outflow is normally closed (e.g. via a clamp in a cassette system), but is automatically opened (e.g. in a pressure-controlled manner via a heparin flush control algorithm) as required. Some of the heparinized flushing solution is thus drained off. Through a suitable control, the heparinized substitution solution can thus dwell in the arterial branch, in the dialyzer and in the venous branch and can be drained off via the UF pump and the outflow. Only the heparinized substitution solution which was not removed by the UF pump and the outflow reaches the patient. The elements of the control algorithm are expanded by a possible outflow clamp. Input parameters for the control algorithm thus, for example, comprise the arterial pressure, the venous pressure and the pressure on the dialyzate side (inflow/outflow). Exemplary output parameters comprise the conveying rate of a blood pump, heparin pump, ultrafiltration pump or substitution pump as well as the control of a venous clamp, arterial clamp or outflow clamp.

In summary it can be stated that the invention provides a method and an apparatus for the fully automatic predialytic anti-clotting priming and intradialytic flushing as well as for the coagulation-inhibiting surface treatment of the extracorporeal circuit in acute and chronic renal replacement therapy, e.g. with HD or HDF methods.

Clotting in extracorporeal circuits and specifically within the framework of a low-heparin or heparin-free dialysis is reduced or prevented. An aspect of the idea relates to an automated two-phase anticoagulation without systemic liquid charging and anticoagulant charging of the patient by priming and flushing. On the one hand, a predialytic flushing of the extracorporeal circuit with heparinized solutions is therefore proposed, and an intermittent flushing of the circuit with heparinized solution with a stopped treatment, on the other hand—to counter the fatigue effect of the priming. A further aspect comprises the extracorporeal circuit being completely filled with the solution and being emptied again after a specific dwell time. A circulation can be omitted in an embodiment. A further core aspect is the automation of the process described in more detail above. In an aspect of the idea in accordance with the invention, the blood flow is greatly reduced or even stopped and the flushing volume is led off via the dialyzer or via an additional outflow so that the patient is only marginally exposed (volume from the hose piece between the outflow and the venous connection).

The invention claimed is:

1. A method of flushing an extracorporeal blood circuit having a venous port, preferably an extracorporeal blood circuit of a dialysis machine, with a flushing liquid, wherein the flushing liquid contains an anticoagulant agent and whereby at least some of the flushing liquid leaves the extracorporeal circuit through an outflow different from the venous port, whereby the extracorporeal blood circuit has a venous or arterial clamp closed at least at times during the method under control of an output parameter of a control algorithm, whereby the clamp is controlled based upon arterial pressure, venous pressure, and pressure on the dialysate side at the inflow, the outflow, or the inflow and the outflow.

2. A method in accordance with claim 1, characterized in that the extracorporeal circuit is completely filled with the flushing liquid; and/or in that the flushing liquid remains stationary in the circuit for a certain dwell time and is optionally moved or is circulated in a short-circuited circuit.

3. A method in accordance with claim 2, characterized in that the dwell time amounts to between 4 and 15 minutes.

4. A method in accordance with claim 2, characterized in that the flushing liquid is displaced from the circuit at the end of the dwell time.

5. A method in accordance with claim 4, characterized in that the displacement takes place using a flushing liquid which likewise contains an anticoagulant agent; or in that the displacement takes place using a flushing liquid which is free of the anticoagulant agent.

6. A method in accordance with claim 4, characterized in that the process of the remaining of the flushing liquid in the circuit and the subsequent displacement is repeated at least twice and optionally several times.

7. A method in accordance with claim 1, characterized in that the extracorporeal blood circuit comprises a dialyzer and the outflow corresponds to the dialyzer; or in that the outflow is arranged in the venous line.

8. A method in accordance with claim 1, characterized in that the flushing liquid is admixed with the anticoagulant agent before or after its entry into the extracorporeal blood circuit.

9. A method in accordance with claim 1, characterized in that the method is carried out within the framework of the priming process.

10. A method in accordance with claim 1, characterized in that the anticoagulant agent is heparin.

11. A method in accordance with claim 3, characterized in that the dwell time amounts to between 8 and 12 minutes.

\* \* \* \* \*